United States Patent
Young et al.

(10) Patent No.: US 6,362,152 B1
(45) Date of Patent: Mar. 26, 2002

(54) LOW COLOR AND LOW HAZE FORMULATIONS OF SODIUM O-PHENYLPHENATE

(75) Inventors: Tracy L. Young, Saginaw; Charles D. Gartner, Midland; Dawn L. Carsten, Midland; Richard W. Walter, Jr., Midland, all of MI (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/544,745

(22) Filed: Apr. 7, 2000

(51) Int. Cl.$^7$ .............. C11D 3/48; C11D 9/42; C11D 17/00
(52) U.S. Cl. ............ 510/386; 510/382; 510/383
(58) Field of Search ............. 510/382, 383, 510/386

(56) References Cited

U.S. PATENT DOCUMENTS

| | | | |
|---|---|---|---|
| 3,002,939 A | 10/1961 | Balassa | 260/6 |
| 3,177,144 A | 4/1965 | Reamer et al. | 252/32.5 |
| 3,503,885 A | 3/1970 | Weddel | 252/105 |
| 3,721,629 A | 3/1973 | Goodenough | 252/105 |
| 3,850,864 A | 11/1974 | Emerson | 260/17.2 |
| 4,716,180 A | 12/1987 | Fetty et al. | 514/782 |
| 5,037,726 A | * 8/1991 | Kojima et al. | 430/378 |
| H972 H | * 10/1991 | Inoue | 430/558 |
| 5,374,378 A | 12/1994 | Lorentzen et al. | 252/380 |
| 5,380,624 A | 1/1995 | Yoshida et al. | 430/372 |
| 5,420,015 A | 5/1995 | Wuerch | 106/162 |
| 5,431,906 A | 7/1995 | Mohseni et al. | 424/73 |
| 5,629,350 A | 5/1997 | Gartner | 514/736 |

FOREIGN PATENT DOCUMENTS

| | | |
|---|---|---|
| CA | 780380 | 3/1968 |
| CA | 938888 | 12/1973 |
| GB | 1226338 | 3/1971 |
| JP | 57-165332 | 10/1982 |
| WO | 97/46218 | 12/1997 |

OTHER PUBLICATIONS

Derwent Abstract, DE 2,063,631 Mixed O–Phenylphenol and higher alkylphen—of disinfectants (1971).
Derwent Abstract, JP 60–58914 External gel prepns. Contg. Imidazole antifungals—do not irritate, spread easily are not sticky and allow imidazole to be absorbed through skin but not to evaporate off. (1985).

* cited by examiner

Primary Examiner—Yogendra N. Gupta
Assistant Examiner—John M Petruncio

(57) ABSTRACT

A color stable aqueous solution containing a relatively high concentration of sodium o-phenylphenate is described where stabilizing components include an oxygen scavenger and a free radical scavenger. The aqueous solutions of NaOPP prepared according to the present invention exhibit an absorbance at 400 nanometers of at most one-half the absorbance exhibited by untreated solutions after incubation for 72 hours at 44° C. and 4 hours under ultraviolet light. The aqueous solution is useful as a concentrate that can be diluted to a desirable antimicrobial concentration level prior to application.

18 Claims, No Drawings

LOW COLOR AND LOW HAZE FORMULATIONS OF SODIUM O-PHENYLPHENATE

TECHNICAL FIELD

The invention relates to concentrated aqueous formulations of a sodium salt of o-phenylphenol. The invention relates more specifically to aqueous formulations that exhibit excellent color stability while containing high concentrations of sodium o-phenylphenate. The invention relates especially to such formulations containing from about 15 to about 75 weight percent of sodium o-phenylphenate.

BACKGROUND OF THE INVENTION

O-phenylphenol (OPP) is well known in the art as an antimicrobial, disinfectant and preservative. Sodium salts of o-phenylphenol are available commercially, for example, as DOWICIDE A and DOWICIDE 25L (from the Dow Chemical Company). NaOPP is described, for example, in U.S. Pat. Nos. 3,503,885; 3,850,864; 5,420,015; and 5,380,624.

NaOPP is frequently provided commercially in the form of a concentrated, aqueous composition. The concentrate is typically diluted to a concentration that is desirable for antimicrobial use. However, concentrated aqueous NaOPP compositions generally exhibit poor color stability. Storage at room temperature, even for a few days, can cause the compositions to turn light brown. With additional time, the compositions can turn dark brown. While the color of the composition does not significantly impact the antimicrobial efficacy of the composition, the color can impart a negative perception to the customer.

In addition to color degradation, aqueous solutions of NaOPP are prone to undergoing additional deleterious processes. Haziness can form as a result of suspended particles. A process known as "oiling-out" can occur in which a non-soluble oily layer can form and either float or sink to the bottom of the product. Sedimentation, or the setting out of solid particles, can also occur.

It is known in the art that compositions containing phenols generally have poor color stability. While approaches for improving the color stability of phenol compositions have been developed, these approaches have generally been designed to improve the color stability of compositions containing relatively low phenol concentrations.

Thus, a need remains for development of aqueous compositions containing high concentrations of NaOPP that exhibit improved color stability.

SUMMARY OF THE INVENTION

The present invention is directed to a color stable aqueous solution that contains a relatively high concentration of sodium o-phenylphenate. The aqueous solutions of NaOPP prepared according to the present invention exhibit an absorbance at 400 nanometers of at most one-half the absorbance exhibited by untreated solutions after incubation for 72 hours at 44° C. and 4 hours under ultraviolet light. The aqueous solution is useful as a concentrate that can be diluted to a desirable antimicrobial concentration level prior to application.

Accordingly, the invention is found in a color-stable concentrate composition containing about 15 to about 75 weight percent sodium o-phenylphenate, about 0.1 to about 5 weight percent of an oxygen scavenger, and about 0.1 to about 2 weight percent of a free radical scavenger selected from the group consisting of N,N-diethylhydroxylamine, N-isopropylhydroxylamine, and hydroxylamine, with the balance being water.

The invention is also found in a color stable composition that includes about 15 to about 75 weight percent of sodium o-phenylphenate, about 0.1 to about 5 weight percent of sodium sulfite, about 0.1 to about 2 weight percent of N,N-diethylhydroxylamine, and up to about 40 weight percent of ethylene glycol or propylene glycol, with the balance being water.

The invention is further directed to a method of preparing a color-stable concentrate solution. The method includes blending or mixing in an aqueous solution of about 15 to about 75 weight percent sodium o-phenylphenate about 0.1 to about 5 weight percent of an oxygen scavenger and about 0.1 to about 2 weight percent of a free radical scavenger selected from the group consisting of N,N-diethylhydroxylamine, N-isopropylhydroxylamine, and hydroxylamine.

The invention is also directed to a method of preparing a color stable concentrate solution that includes the steps of reacting in-situ o-phenylphenol and sodium hydroxide in an aqueous solution, in amounts necessary to prepare about 15 to about 75 weight percent sodium o-phenylphenate. The aqueous solution also includes about 0.1 to about 5 weight percent of an oxygen scavenger and about 0.1 to about 2 weight percent of a free radical scavenger selected from the group consisting of N,N-diethylhydroxylamine, N-isopropylhydroxyl-amine, and hydroxylamine.

DETAILED DESCRIPTION OF THE INVENTION

The aqueous concentrate compositions described herein exhibit excellent color stability. While prior art compositions containing relatively high levels of sodium o-phenylphenate are prone to color degradation or instability, the compositions espoused by the invention exhibit substantially reduced levels of color degradation or instability. We have found that the inclusion of several adjuvants result in a composition with desirable color stability performance. Specifically, we have found oxygen scavengers and free radical scavengers to be quite useful We have found that the use of solubilizers can be beneficial in helping to solubilize otherwise insoluble degradation products of the sodium o-phenylphenate.

As used herein, the term "oxygen scavenger" is used to describe compounds that can absorb, neutralize or otherwise remove oxygen from solution. It is believed that molecular oxygen, if not removed, can react with o-phenylphenol and sodium salts thereof to form color bodies. Oxygen scavengers are also known as antioxidants. A wide number of oxygen scavengers are known in the art. Examples of oxygen scavengers suitable for use herein include sodium sulfite, sodium pyrosulfite, sodium thiosulfate, sodium dithionite and sodium hypophosphite. Preferred oxygen scavengers include sodium sulfite.

The sodium o-phenylphenate compositions of the invention include about 0.1 to about 5 weight percent of an oxygen scavenger. Preferably, the oxygen scavenger is present in the composition at a concentration of about 0.5 to about 1.0 weight percent. All compositions discussed herein are described in terms of weight percent, based upon the total weight of the composition.

The term "free radical scavenger" refers to compounds that can absorb, neutralize or otherwise remove free radicals from the compositions of the invention. A free radical scavenger can remove free radicals that would otherwise participate in degradation reactions. Free radicals can be generated via thermal or light induction. A number of free radical scavengers are known to those of skill in the art. Useful free radical scavengers are hydroxylamines, for example. A preferred free radical scavenger is N,N-diethylhydroxylamnine. The compositions of the invention contain about 0.1 to about 2 weight percent of a free radical scavenger.

The compositions of the invention may also include a solubilizer that can function to solubilize non-water soluble sodium o-phenylphenoate degradation products. Solubilizing the degradation products helps to prevent components from separating, thereby reducing visible haze. Examples of useful solubilizers include alkylene diols such as ethylene glycol and propylene glycol. Solubilizers can be present at a concentration as high as 40 weight percent. Preferably, the compositions of the invention contain about 5 to about 10 weight percent of a solubilizer.

Another optional component is a metal ion scavenger or chelant. These are used to complex with metal ions in solution, thereby preventing the ions from catalyzing reactions between oxygen and sodium o-phenylphenate or other organic materials. Examples of useful chelants are triethanolamine and aminocarboxylates such as ethylenediaminetetraacetic acid (EDTA), especially tetrasodium EDTA. If used, the metal ion scavenger or chelant is present at a concentration of about 0.01 to about 2 weight percent. Preferably, the chelant is present at a concentration of about 0.01 to 0.05 weight percent.

The compositions of the invention are substantially aqueous, containing from about 25 to about 80 weight percent water. Preferably, the compositions contain about 70 to about 80 weight percent water.

The useful and preferred compositions according to the invention are summarized in the table below:

| Component | Useful Range (weight percent) | Preferred Range (weight percent) |
|---|---|---|
| sodium o-phenylphenate | 15–75 | 20–40 |
| oxygen scavenger | 0.1–5 | 0.5–2 |
| free radical scavenger | 0.1–2 | 0.25–1.5 |
| solubilizer | 0–40 | 5–10 |
| chelating agent | 0.01–2 | 0.1–0.5 |
| water | balance | balance |

The concentrate composition can be generally prepared by starting with o-phenylphenol, which is reacted with sodium hydroxide to form sodium o-phenylphenate. The solid sodium o-phenylphenate is isolated, and adjuvants can be incorporated into the solid by blending with the solid. Alternatively, the adjuvants can be mixed into the reaction mixture.

Alternatively, the compositions of the invention can be formed in an in-situ process in which o-phenylphenol is reacted with sodium hydroxide in an aqueous solution that also contains the desired adjuvants. In this process, no solid intermediate is produced or isolated.

As another alternative, the compositions of the invention can be formed by starting with sodium o-phenylphenate or any hydrated form of sodium o-phenylphenate. The composition can be formed by blending and dissolving the desired components.

Once formed, the concentrate composition is preferably diluted by the customer for use in a variety of possible antimicrobial applications. The concentrate can be diluted with water or another solvent or can be mixed directly into an intended end use application. The final sodium o-phenylphenate concentration as employed in the end use application will vary depending on the nature of the application. Preferably, the final NaOPP concentration will be at least about 100 ppm, and more preferably, at least about 500 ppm. Preferably, the final NaOPP concentration will be no more than about 10,000 ppm, and more preferably no more than about 5000 ppm.

Typical end use applications for NaOPP include paints, inks, adhesives, soaps, cutting oils, textiles, lotions and shampoos. Typical industrial end uses can include processes which employ aqueous transport and supply streams, such as processes for manufacturing feedstocks and paper and pigment slurries.

The following example is intended to illustrate the invention but are not to be construed as limiting the invention in any manner.

EXAMPLES

Aqueous solutions of sodium o-phenylphenate were prepared including the additive combinations shown below in Tables 1 and 2. The samples were aged in a 44° C. oven and under a long wavelength ultraviolet lamp to accelerate color development. Absorbance was measured at 400 nanometers using a Spectronic 21. Solutions of varying concentrations of Mordant Brown #24 were used as a color reference standard. A 50 ppm solution of Mordant Brown #24 is light brown and has an absorbance of 0.33. At concentrations greater than 300 ppm of Mordant Brown #24, the solution becomes dark brown or black. The absorbance of a 1000 ppm solution of Mordant Brown #24 is 6.24.

As shown in Tables 1 and 2, the addition of N,N-diethylhydroxylamnue, sodium sulfite, triethanolamine and propylene glycol reduced the color development of the solutions aged both in the oven and with exposure to ultraviolet light. The combination of these additives or adjuvants decreased color development most dramatically, especially for solutions that were exposed to ultraviolet light and that had prolonged storage periods.

The compositions shown in Table 1 represent a 25 percent aqueous solution of NaOPP in conjunction with the specifically identified additives or adjuvants. The compositions shown in Table 2 represent a 25 percent aqueous solution of NaOPP with 5 percent propylene glycol, 500 ppm of N,N-diethylhydroxylamine, in conjunction with the specifically identified additives or adjuvants.

TABLE 1

| Sample # | Additives | Absorbance at 400 nm | | Solution Color |
|---|---|---|---|---|
| | | 72 hours @ 44° C. | 72 hours @ 44° C., 4 hours UV | |
| 1 | control-no additives | 0.59 | 0.99 | dark brown |
| 2 | 5% propylene glycol | 0.32 | 0.67 | dark golden-brown |
| 3 | 5% propylene glycol<br>5000 ppm sodium sulfite | 0.17 | 0.38 | golden brown |
| 4 | 5% propylene glycol<br>1000 ppm N,N-diethylhydroxylamine | 0.05 | 0.23 | colorless, light yellow tint |
| 5 | 5% propylene glycol<br>500 ppm tetrasodium EDTA<br>5000 ppm sodium sulfite | 0.18 | 0.37 | golden brown |
| 6 | 5% propylene glycol<br>100 ppm triethanolamine<br>500 ppm N,N-diethylhydroxylamine<br>500 ppm tetrasodium EDTA<br>5000 ppm sodium sulfite | 0.06 | 0.19 | colorless, light yellow tint |
| 7 | 4.5% propylene glycol<br>100 ppm triethanolamine<br>1000 ppm N,N-diethylhydroxylamine<br>10,000 ppm sodium sulfite | 0.06 | 0.19 | colorless, light yellow tint |

TABLE 2

| No. | Additives | Absorbance at 400 nm | | |
|---|---|---|---|---|
| | | 72 hours @ 44° C., 4 hours UV | Oven/UV/RT[1] | Oven/RT[2] |
| 1 | control-no additional additives | 0.92 | 13.80 dark black | 10.40 dark black |
| 2 | 100 ppm triethanolamine | 0.87 | 7.35 dark black | 8.48 dark black |
| 3 | 500 ppm tetrasodium EDTA | — | 15.08 dark black | 16.32 dark black |
| 4 | 2500 ppm sodium sulfite | 0.50 | 4.73 dark brown | 3.73 dark brown |
| 5 | 5000 ppm sodium sulfite | 0.42 | 3.90 reddish brown | 2.88 reddish brown |
| 6 | 50 ppm triethanolamine<br>100 ppm tetrasodium EDTA | 0.87 | 10.76 dark black | 9.76 dark black |
| 7 | 50 ppm triethanolamine<br>100 ppm tetrasodium EDTA<br>5000 ppm sodium sulfite | 0.39 | 3.32 reddish brown | 2.32 dark golden brown |
| 8 | 100 ppm triethanolamine<br>500 ppm tetrasodium EDTA<br>5000 ppm sodium sulfite | 0.28 | 2.69 reddish brown | 1.70 dark golden brown |

1. 192 hours at 44° C. in oven, 20 hours UV, 1 month benchtop at room temperature.
2. 192 hours at 44° C. in oven, 1 month benchtop at room temperature.

The above specification, example and data provide a clear basis for understanding the operation of the compositions and methods of the invention. While the invention can be embodied in a variety of specific examples and processes, the invention resides in the claims hereinafter appended.

What is claimed is:

1. A color-stable concentrate composition comprising:
  about 15 to about 75 weight percent sodium o-phenylphenate based upon the total weight of the composition;
  about 0.1 to about 5 weight percent of an oxygen scavenger;
  about 0.1 to about 2 weight percent of a free radical scavenger selected from the group consisting of N,N-diethylhydroxylamine, N-isopropylhydroxylamine, and hydroxylamine; and
  the balance being water.

2. The composition of claim 1, having after incubation of 72 hours at 44° C. and 4 hours under ultraviolet light an absorbance at 400 nanometers of one-half or less than that of a composition differing only in the absence of said oxygen scavenger and said free radical scavenger.

3. The composition of claim 1, wherein the composition comprises about 20 to about 30 weight percent sodium o-phenylphenate based upon the total weight of the composition.

4. The composition of claim 1, wherein the composition further. comprises about 0.01 to about 2 weight percent triethanolamine.

5. The composition of claim 1, wherein the composition further comprises up to about 40 weight percent of a solubilizer based upon the total weight of the composition.

6. The composition of claim 1, wherein the composition further comprises up to about 40 weight percent of a solubilizer and about 0.01 to about 2 weight percent triethanolamine based upon the total weight of the composition.

7. The composition of claim 1, wherein the oxygen scavenger is selected from the group consisting of sodium sulfite, sodium pyrosulfite, sodium thiosulfate, sodium dithionite and sodium hypophosphite.

8. The composition of claim 7, wherein the oxygen scavenger is sodium sulfite.

9. The composition of claim 1, wherein the free radical scavenger is N,N-diethylhydroxyamine.

10. The composition of claim 1, wherein the solubilizer is an alkylene diol.

11. The composition of claim 10, wherein the alkylene diol is ethylene or propylene glycol.

12. A color stable composition comprising:
   about 15 to about 75 weight percent of sodium o-phenylphenate;
   about 0.1 to about 5 weight percent of sodium sulfite;
   about 0.1 to about 2 weight percent of N,N-diethylhydroxylamine;
   up to about 40 weight percent of ethylene glycol or propylene glycol, and the balance being water.

13. A method of preparing a color-stable concentrate solution comprising blending or mixing in an aqueous solution of about 15 to about 75 weight percent sodium o-phenylphenate about 0.1 to about 5 weight percent of an oxygen scavenger and about 0.1 to about 2 weight percent of a free radical scavenger selected from the group consisting of N,N-diethylhydroxylamine, N-isopropylhydroxylamine, and hydroxylamine.

14. The method of claim 13, wherein the concentrate, after incubation of 72 hours at 44° C. and 4 hours under ultraviolet light, has an absorbance at 400 nanometers of one-half or less than that of the initial absorbance prior to incubation.

15. The method of claim 13, wherein about 0.01 to about 2 weight percent triethanolamine is added to the aqueous solution.

16. The method of claim 13, wherein up to about 40 weight percent of a solubilizer is added in the aqueous solution.

17. A method of preparing a color stable concentrate solution comprising:
   reacting in-situ o-phenylphenol and sodium hydroxide in an aqueous solution, in amounts necessary to prepare about 15 to about 75 weight percent sodium ortho-phenylphenate, which aqueous solution further comprises:
      (a) about 0.1 to about 5 weight percent of an oxygen scavenger; and
      (b) about 0.1 to about 2 weight percent of a free radical scavenger selected from the group consisting of N,N-diethylhydroxylamine and hydroxylamine.

18. The method of claim 17, wherein the aqueous solution further comprises about 0.01 to about 2 weight percent triethanolamine and up to about 40 weight percent of a solubilizer.

* * * * *